United States Patent
Zeng et al.

(10) Patent No.: US 10,035,745 B1
(45) Date of Patent: Jul. 31, 2018

(54) METHODS OF PURIFYING CRUDE SEVOFLURANE

(71) Applicants: BAXTER INTERNATIONAL INC., Deerfield, IL (US); BAXTER HEALTHCARE SA, Glattpark (Opfikon) (CH)

(72) Inventors: Yongxian Zeng, Libertyville, IL (US); Hong-Chang Lee, Libertyville, IL (US); Linas Kudzma, Annandale, NJ (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 0 days.

(21) Appl. No.: 15/224,542

(22) Filed: Jul. 30, 2016

(51) Int. Cl.
C07C 41/34 (2006.01)
C07C 41/42 (2006.01)

(52) U.S. Cl.
CPC .............. *C07C 41/42* (2013.01); *C07C 41/34* (2013.01)

(58) Field of Classification Search
None
See application file for complete search history.

(56) References Cited

U.S. PATENT DOCUMENTS

| | | | |
|---|---|---|---|
| 2,805,262 A * | 9/1957 | Wilson | C07C 41/44 203/33 |
| 5,679,576 A | 10/1997 | Kawai et al. | |
| 5,684,211 A | 11/1997 | Kawai et al. | |
| 6,448,451 B1 | 9/2002 | Rudzinski et al. | |
| 7,230,142 B1 | 6/2007 | Kawai et al. | |
| 7,732,647 B2 | 6/2010 | Jones et al. | |
| 8,729,313 B2 | 5/2014 | Kudzma et al. | |
| 2009/0171128 A1* | 7/2009 | Jones | C07C 41/01 568/683 |

FOREIGN PATENT DOCUMENTS

WO WO-2004/065430 8/2004

OTHER PUBLICATIONS

Goldberg et al., Dose of compound A, not sevoflurane, determines changes in the biochemical markers of renal injury in healthy volunteers, Anesth. Analg., 88(2):437-45 (1999).

* cited by examiner

*Primary Examiner* — Rosalynd A Keys
(74) *Attorney, Agent, or Firm* — Marshall, Gerstein & Borun LLP

(57) ABSTRACT

A method of purifying crude sevoflurane comprising (i) providing crude sevoflurane and an aqueous base to a first centrifugal separator, wherein the crude sevoflurane comprises sevoflurane and hexafluoroisopropanol; (ii) mixing the crude sevoflurane and the aqueous base in the first centrifugal separator; and (iii) separating the sevoflurane from the aqueous base in the first centrifugal separator, thereby purifying the crude sevoflurane.

16 Claims, 2 Drawing Sheets

METHODS OF PURIFYING CRUDE SEVOFLURANE

FIELD OF THE DISCLOSURE

The disclosure relates generally to methods of purifying crude sevoflurane (1,1,1,3,3,3-hexafluoro-2-(fluoromethoxy)propane). More particularly, the disclosure is directed to methods of purifying of crude sevoflurane prior to final distillation and packaging.

BRIEF DESCRIPTION OF RELATED TECHNOLOGY

Sevoflurane is a halogenated, volatile anesthetic typically administered by inhalation to induce and/or maintain general anesthesia. As generally disclosed in WO 2004/065430, sevoflurane can be produced by a number of synthetic routes, each of which rely on the use of hexafluoroisopropanol ("HFIP") as a starting material.

HFIP is difficult to separate from sevoflurane because it has a similar boiling point and may form an azeotrope with sevoflurane. U.S. Pat. No. 5,679,576 ("the '576 patent") describes a process in which crude sevoflurane is contacted with an alkali aqueous solution and/or water to dissolve and remove unreacted hexafluoroisopropanol ("HFIP") from the crude sevoflurane. The '576 patent further discloses that sevoflurane decomposition products, such as 1,1,3,3,3-pentafluoro-2-(fluoromethoxy)prop-1-ene (i.e., "compound A"), can form. Compound A has been shown to induce renal injury in rats and to produce transient renal injury in humans (Goldberg, et al., Anesth. Analg., 88:437-45 (1999)). Thus, it is desirable to sufficiently minimize the quantity of compound A to ensure the quality of sevoflurane. However, compound A has a boiling point close to that of sevoflurane such that it is not practical to effectively separate or quantitate sevoflurane and compound A using distillation or a gas chromatograph equipped with a conventional column. The '576 patent discloses using a capillary column comprising cross-linked cyanopropylmethylphenylsilicone to effectively separate sevoflurane from compound A so as to allow adequate quality control monitoring of sevoflurane production. In view of the information obtained via the capillary column, continuous monitoring and adjustment of various process parameters can be performed to ensure sevoflurane quality.

U.S. Pat. No. 5,684,211 ("the '211 patent") discloses that distilling sevoflurane causes the decomposition of sevoflurane and compound A formation. The '211 patent further discloses that the decomposition of sevoflurane and accompanying compound A formation are suppressed by adding an alkali metal compound such as an alkali metal hydroxide, alkali metal hydrogen phosphate, alkali metal phosphates, alkali metal hydrogen carbonates, alkali metal borate, alkali metal sulfite, and the like during distillation.

U.S. Pat. No. 7,230,142 ("the '142 patent") discloses removing HFIP from sevoflurane by contacting sevoflurane with a basic aqueous solution comprising a hydroxide, oxide, or carbonate. The '142 patent discloses that sodium hydroxide and/or potassium hydroxide are preferred.

U.S. Pat. No. 7,732,647 ("the '647 patent") discloses washing crude sevoflurane with water, separating the resulting organic and aqueous phases without fractional distillation, and repeatedly washing the organic phase containing sevoflurane with water and separating the resulting organic and aqueous phases as needed until purified sevoflurane comprising no more than an acceptable amount of HFIP is isolated.

In view of the foregoing, it can be seen that methods of purifying sevoflurane can be time consuming, energy intensive, and/or subject to human error.

SUMMARY

In one embodiment, the invention provides a method of purifying crude sevoflurane comprising (i) providing crude sevoflurane and an aqueous base to a first centrifugal separator, wherein the crude sevoflurane comprises sevoflurane and hexafluoroisopropanol; (ii) mixing the crude sevoflurane and the aqueous base in the first centrifugal separator; and (iii) separating the sevoflurane from the aqueous base in the first centrifugal separator, thereby purifying the crude sevoflurane.

In another embodiment, the invention provides a method of purifying crude sevoflurane comprising (i) providing crude sevoflurane and an aqueous base to a first in-line mixer, wherein the crude sevoflurane comprises sevoflurane and hexafluoroisopropanol; (ii) mixing the crude sevoflurane and the aqueous base in the first in-line mixer to form a first mixture; (iii) providing the first mixture to a first centrifugal separator; and (iv) separating the sevoflurane from the aqueous base in the first centrifugal separator, thereby purifying the crude sevoflurane.

DETAILED DESCRIPTION

Figure 1:
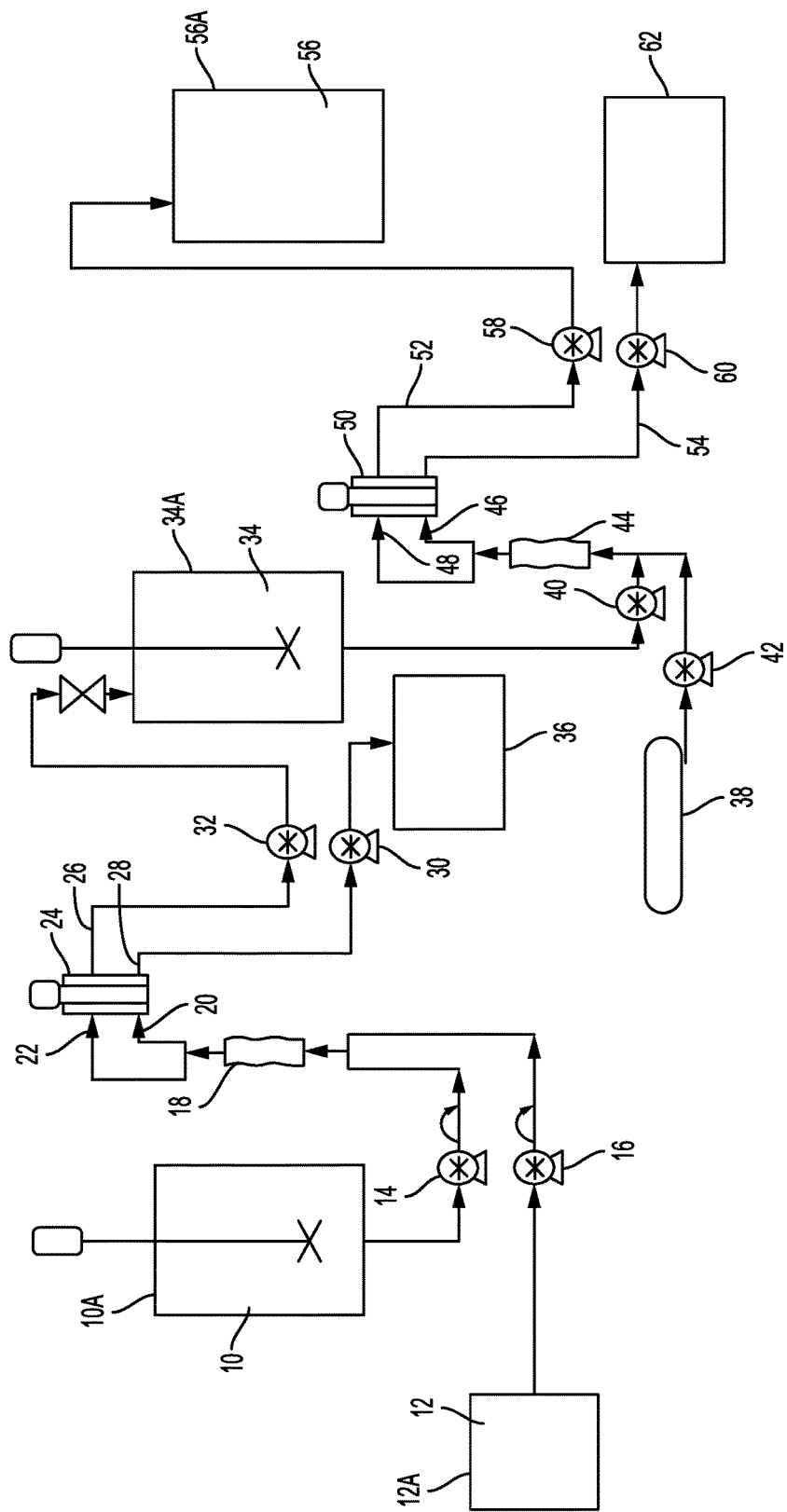
FIG. 1 illustrates an exemplary process flow diagram for purifying sevoflurane according to the methods of the invention.

The present invention is generally directed to methods of purifying crude sevoflurane in which a centrifugal separator is used to "wash" and remove impurities such as HFIP from crude sevoflurane. The disclosed methods mix a first organic stream comprising crude sevoflurane and a second aqueous stream comprising a base and then separate the organic phase containing sevoflurane from the aqueous phase containing base in a centrifugal separator. Centrifugal separators utilize the force generated by rotating a fluid about a central axis to separate fluids having different densities. In one embodiment, the aqueous and organic phases can be introduced into the centrifugal separator via an in-line mixer where the two phases are mixed relatively quickly, but sufficiently thoroughly, to allow substantially complete conversion of HFIP to the corresponding HFIP salt, such that substantially complete removal of HFIP can be effected (because of the solubility of its salt in the aqueous phase). Surprisingly, despite the relatively short contact time between crude sevoflurane and an aqueous base in the methods disclosed herein, HFIP is effectively removed from the crude sevoflurane and impurity formation, particularly formation of compound A, is advantageously minimized often to an undetectable level. As a result, because compound A is the major impurity that has to be removed during the final distillation, the methods according to the invention advantageously facilitate sevoflurane production in less time and in high yield and purity relative to existing sevoflurane purification processes. Indeed, the methods of purifying crude sevoflurane according to the invention have been demonstrated to increase capacity for purified sevoflurane production by over 50% (primarily due to less time needed in the final distillation step), the yield by about 20%, and the time needed to accomplish washing of the sevoflurane from hours to seconds relative to a method incorporating various purification steps disclosed in the prior art discussed in the Background section above as shown in the Example section below.

In addition, the methods according to the invention can be operated in a continuous mode and automatically controlled without any manual operation. Furthermore, by using a centrifugal separator alone or in combination with an in-line mixer, the methods according to the invention advantageously enable mixing and phase separation in significantly fewer process steps and in significantly less time than the comparative method exemplified in the Example section below.

As used herein, "crude sevoflurane" refers to sevoflurane containing impurities such as HFIP and/or compound A in total amounts greater than 0.03 weight percent, for example, greater than 0.1 weight percent. As non-limiting examples, crude sevoflurane may contain about 5 weight percent HFIP and/or about 300 ppm compound A. On the other hand, as used herein, "pharmaceutical-grade sevoflurane" contains less than 300 ppm of total impurities, less than 100 ppm of any single impurity, and less than 25 ppm compound A. In a preferred aspect, pharmaceutical-grade sevoflurane purified according to the methods of the invention contains less than 10 ppm compound A.

In one embodiment, the invention provides a method of purifying crude sevoflurane comprising (i) providing crude sevoflurane and an aqueous base to a first centrifugal separator, wherein the crude sevoflurane comprises sevoflurane and hexafluoroisopropanol; (ii) mixing the crude sevoflurane and the aqueous base in the first centrifugal separator; and (iii) separating the sevoflurane from the aqueous base in the first centrifugal separator, thereby purifying the crude sevoflurane. Mixing of the crude sevoflurane and the aqueous base can be performed in the centrifugal separator to convert the hexafluoroisopropanol contained in the crude sevoflurane to a water-soluble hexafluoroisopropanoxide salt, such that substantially complete removal of HFIP can be effected (because of the solubility of its salt in the aqueous phase).

According to this embodiment, the crude sevoflurane and the aqueous base can be provided to the first centrifugal separator, for example, by pumping the crude sevoflurane into the heavy phase inlet of the centrifugal separator and the aqueous base into the light phase inlet of the centrifugal separator. Thereafter, the sevoflurane separated from the aqueous base in the first centrifugal separator and additional water can be provided to a second centrifugal separator, for example, by pumping the sevoflurane separated from the aqueous base into a heavy phase inlet of the second centrifugal separator and the additional water into a light phase inlet of the second centrifugal separator. Mixing of the sevoflurane separated from the aqueous base and additional water can be performed in the second centrifugal separator to remove residual aqueous base from the sevoflurane, and separation of substantially purified sevoflurane from the water can also be conducted substantially simultaneously in the second centrifugal separator.

Alternatively, according to this embodiment, the sevoflurane separated from the aqueous base and additional water can be provided to an in-line mixer, which is typically a pipe containing mixing elements on its interior surface that is incorporated into the process line, and then mixed in the in-line mixer, typically by pumping the fluids to, into, and through the in-line mixer such that the two fluids are mixed as they are pumped through the process line, prior to the resulting mixture being provided to the second centrifugal separator. The mixing in the in-line mixer is generally conducted to remove residual aqueous base from the sevoflurane. In this aspect of the foregoing embodiment, the resulting mixture of the sevoflurane separated from the aqueous base and the additional water can then be provided to the second centrifugal separator by pumping the (already mixed) sevoflurane and additional water into one or more of a heavy phase inlet and a light phase inlet of the second centrifugal separator and substantially purified sevoflurane can be separated from the water in the second centrifugal separator. Typically, the mixture of the sevoflurane separated from the aqueous base and the additional water is pumped into both inlets of the second centrifugal separator, but it is also possible, for example, to pump the resulting mixture into the heavy phase inlet and to simultaneously pump additional water into the light phase inlet of the second centrifugal separator.

In another embodiment, the invention provides a method of purifying crude sevoflurane comprising (i) providing crude sevoflurane and an aqueous base to a first in-line mixer, wherein the crude sevoflurane comprises sevoflurane and hexafluoroisopropanol; (ii) mixing the crude sevoflurane and the aqueous base in the first in-line mixer to form a first mixture; (iii) providing the first mixture to a first centrifugal separator; and (iv) separating the sevoflurane from the aqueous base in the first centrifugal separator, thereby purifying the crude sevoflurane. Mixing of the crude sevoflurane and the aqueous base can be performed in the in-line mixer to convert the hexafluoroisopropanol contained in the crude sevoflurane to a water-soluble hexafluoroisopropanoxide salt, such that substantially complete removal of HFIP can be effected (because of the solubility of its salt in the aqueous phase).

According to this embodiment, the crude sevoflurane and the aqueous base can be provided to the first in-line mixer, which is a typically pipe containing mixing elements on its interior surface that is incorporated into the process line, and then mixed in the first in-line mixer, typically by pumping the crude sevoflurane and the aqueous base to, into, and through the first in-line mixer such that the two fluids are mixed as they are pumped through the process line. In the foregoing embodiment, the mixture of crude sevoflurane and the aqueous base can be provided to the first centrifugal separator by pumping the already mixed crude sevoflurane and the aqueous base into one or more of a heavy phase inlet and a light phase inlet of the first centrifugal separator. Typically, the mixture of crude sevoflurane and aqueous base is pumped into both inlets of the first centrifugal separator, but it is also possible, for example, to pump the mixture into the heavy phase inlet and to simultaneously pump additional water into the light phase inlet of the first centrifugal separator.

Subsequent to separating the sevoflurane from the aqueous base in the first centrifugal separator, the sevoflurane and additional water can be provided to a second centrifugal separator, for example, by pumping the sevoflurane separated from the aqueous base into a heavy phase inlet of the second centrifugal separator and the additional water into a light phase inlet of the second centrifugal separator. Mixing of the sevoflurane separated from the aqueous base and additional water can be performed in the second centrifugal separator to remove residual aqueous base from the sevoflurane, and separation of the sevoflurane from the water can also be conducted substantially simultaneously in the second centrifugal separator.

Alternatively, after the sevoflurane is separated from the aqueous base in the first centrifugal separator, the sevoflurane and additional water can be provided to a second in-line mixer and the sevoflurane can be mixed with the water in the second in-line mixer to form a second mixture. The mixing in the second in-line mixer is generally conducted to remove any residual aqueous base from the sevoflurane. At this point, the second mixture can be provided to a second centrifugal separator by pumping the already mixed sevoflurane and additional water into one or more of a heavy phase inlet and a light phase inlet of the second centrifugal separator and the sevoflurane can be separated from the water in the second centrifugal separator. Typically, the mixture of the sevoflurane separated from the aqueous base and the additional water is pumped into both inlets of the second centrifugal separator, but it is also possible, for example, to pump the mixture into the heavy phase inlet and to simultaneously pump additional water into the light phase inlet of the second centrifugal separator.

In each of the foregoing embodiments, the aqueous base can comprise one or more of sodium hydroxide, potassium hydroxide, calcium hydroxide, ammonium hydroxide, and/or any other water soluble base. Generally, in each of the foregoing embodiments, the concentration of the base can be any concentration up to a saturated concentration. For example, with respect to sodium hydroxide, the concentration can be between about 10 weight percent and about 50 weight percent. Typically, in each of the foregoing embodiments, the volume of sevoflurane to aqueous base is between 10:1 and 1:1, for example, about 2:1, when the aqueous base comprises about 10 wt.% NaOH, but other volume of sevoflurane to aqueous base ratios, other base concentrations, and other bases may be used as long as the amount of base is sufficient to convert the HFIP in the crude sevoflurane to a water-soluble salt such as sodium hexafluoroisopropanoxide, potassium hexafluoroisopropanoxide, calcium hexafluoroisopropanoxide, ammonium hexafluoroisopropanoxide and the like. For example, the volume of sevoflurane to aqueous base ratio may be easily adjusted depending on the base concentration.

In each of the foregoing embodiments, after washing the crude sevoflurane with the aqueous base and then optionally further washing with water, the sevoflurane can be distilled.

In each of the foregoing embodiments, the crude sevoflurane that is washed with the aqueous base and then optionally further washed with water can be provided by first flash distilling a reaction product obtained by synthesizing sevoflurane, for example, according to a known synthetic method, for example, a synthetic method disclosed in WO 2004/065430, which is hereby incorporated herein by reference.

FIG. 1 illustrates a representative embodiment according to the present invention. As shown in FIG. 1, the streams of aqueous base (or caustic solution) 10 and crude sevoflurane 12 are separately pumped using pumps 14, 16 from their respective storage tanks 10A, 12A into the inlets 20, 22 of the first centrifugal separator 24 via an in-line mixer 18. The two streams of aqueous base and crude sevoflurane 10, 12 experience fast, thorough mixing to enable substantially complete HFIP conversion to the HFIP salt in in-line mixer 18. After entering the first centrifugal separator 24, the organic and aqueous phases are quickly and effectively separated and automatically flow out of the first centrifugal separator 24 from designated outlets 26, 28, respectively, for the heavy phase (organic phase comprising the sevoflurane washed with aqueous base 34) and the light phase (aqueous phase comprising the base). The organic phase stream comprising the sevoflurane washed with aqueous base 34 is transferred via pump 32 to an intermediate holding tank 34A. The aqueous phase stream from the first centrifugal separator 24 can be directed to a waste water treatment area 36 via pump 30 to allow recovery of the HFIP dissolved therein.

The sevoflurane washed with aqueous base 34, together with a fresh water stream 38, then are pumped using pumps 40, 42 into the inlets 46, 48 of the second centrifugal separator 50 via a second in-line mixer 44. The two streams of water and sevoflurane previously washed with aqueous base 34, 38 experience fast, thorough mixing to effect substantially complete extraction of any residual aqueous base from the sevoflurane into the additional water in the in-line mixer 44. After entering the second centrifugal separator 50, the organic and aqueous phases are quickly and effectively separated and automatically flow out of the second centrifugal separator 50 from designated outlets 52, 54, respectively, for the heavy phase (organic phase comprising the sevoflurane) and the light phase (aqueous phase comprising water and any residual base). The organic phase stream comprising the sevoflurane 56 is transferred via pump 58 to a holding tank 56A. The aqueous phase stream from the second centrifugal separator 50 can be directed to a waste water treatment area 62 via pump 60 to allow proper treatment and disposal thereof.

Any pump allowing for continuous operation is preferred, for example, peristaltic pumps can be used in the methods according to the invention. Diaphragm pumps may also be used but are piston pumps and thus result in non-continuous flows.

Figure 2:
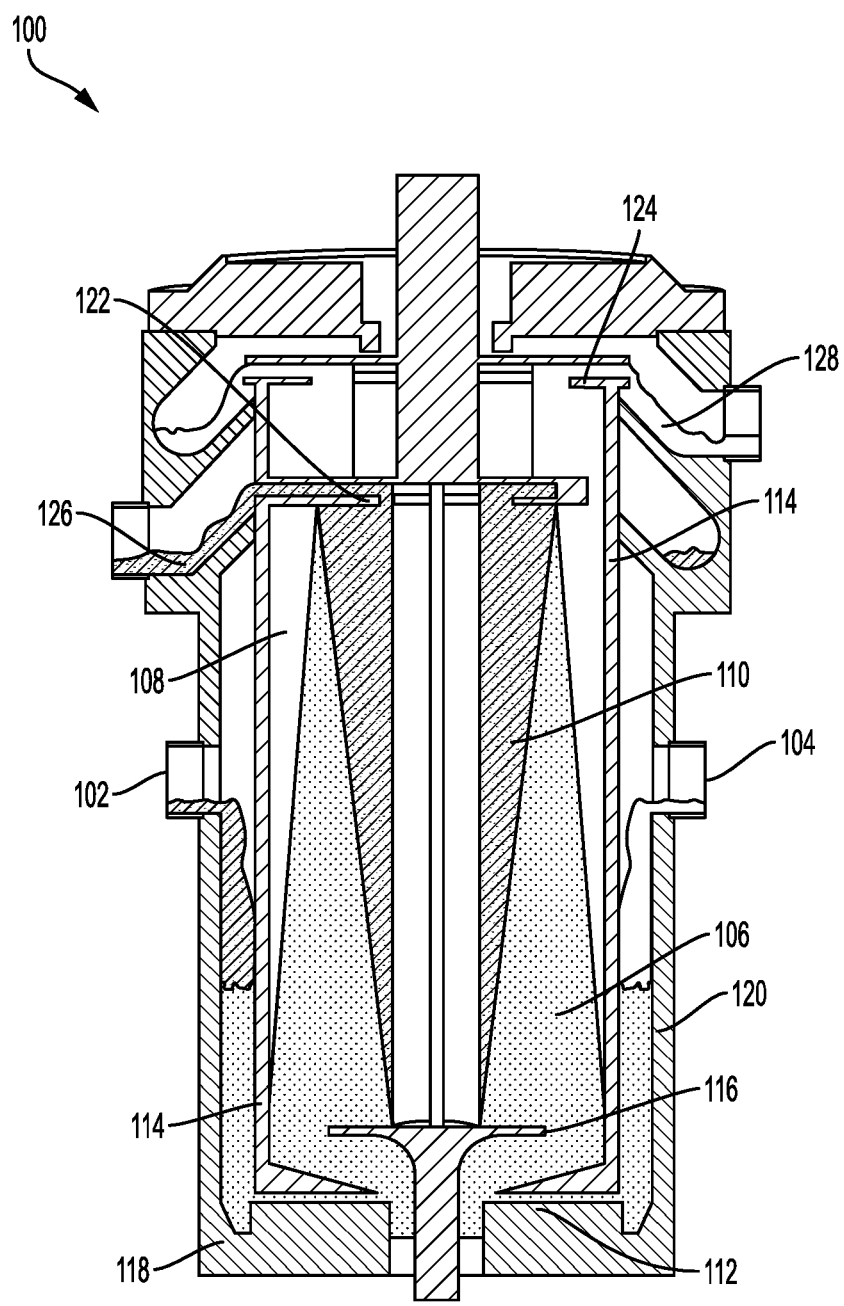
FIG. 2 generally illustrates a centrifugal separator suitable for use in the methods of the invention.

As explained above, centrifugal separators utilize the force generated by rotating a fluid about a central axis to separate fluids having different densities. By spinning two fluids of different densities within a rotating container or rotor, the heavier fluid is forced to the wall at the inside of the rotor while the lighter fluid is forced toward the center of the rotor, thereby allowing the fluids to be separated efficiently and automatically. FIG. 2 generally illustrates how liquid-liquid separation occurs within the centrifugal separator 100, which shares a common structure and is used in substantially the same way as the centrifugal separators 24, 50 illustrated in FIG. 1. In the methods according to the invention, the fluid 106 to be separated typically enters the centrifugal separators 100 already mixed (i.e., the crude sevoflurane and the aqueous base have already been thoroughly mixed via the in-line mixer 18 or 44) through one or both inlets 102, 104. Alternatively, the crude sevoflurane and the aqueous base can be directly fed to the inlets 102, 104, without using an in line-mixer 18, 44, and be rapidly mixed in the annular space between the spinning rotor 114 and stationary housing 120.

After entry into the inlets 102, 104, the mixed fluid 106 is then fed through a rotor inlet 112 at the bottom of the rotor 114. Mixed fluid 106 is shown at the bottom of the centrifugal separator 100. A diverter plate or disk 116 and radial vanes 118 in the housing base 120 direct the mixed fluid 106 to the inside of the rotor 114. As the mixed fluid 106 enters the central opening of the rotor, the mixed fluid 106 is accelerated towards an inside wall of the rotor 114, with separation occurring such that the heavier fluid 108 (i.e., the organic phase containing sevoflurane in the methods according to the invention) is forced to the inside wall of the rotor 114 while the lighter fluid 110 (i.e., the aqueous phase in the methods according to the invention) is forced toward a center of the rotor 114. A lighter phase weir 122 and a heavier phase weir 124 at the top of the rotor allow each phase to exit the rotor 114 via collectors leading to a lighter phase outlet 126 and a heavier phase outlet 128, respectively. The lighter fluid 110 flows toward the center of the rotor 114 where it exits the rotor 114 over the lighter phase weir 122 through the lighter phase outlet 126. The heavier fluid 108 continues up the rotor 114 along the inside wall of the rotor 114 and then exits over the heavy phase weir 124 through the heavier phase outlet 128.

Certain process parameters can impact the purity of the sevoflurane obtained according to the methods according to the invention. Specifically, the heavier phase weir size, centrifugal separator RPM, stream flow rate, and the length of in-line mixer can potentially demonstrate significant impact on separation performance and the purity of the sevoflurane purified in accordance with the methods according to the invention. Generally, it should be expressly noted that process parameters can vary depending on the maximum flowrate of the centrifugal separator and that suitable process parameter values can be determined by one having ordinary skill in the art using routine experimentation. Notwithstanding the foregoing, suitable ranges and/or specific values are provided for exemplary centrifugal separators that may be used in the methods according to the invention. In this respect, centrifugal separators can be manufactured with a variety of flowrates. An exemplary centrifugal separator has a maximum flowrate of 0.5 gpm (1.9 liters/minute). Another exemplary centrifugal separator has a maximum flowrate of 30 gpm (117 liters/minute). In the foregoing centrifugal separators, the heavier phase weir size is adjustable, while the lighter phase weir size is fixed.

Heavier phase weir size (for both the aqueous base washing operation and the water washing operation): For the centrifugal separator having a maximum flowrate of 0.5 gpm, ranges of about 0.8-1.25 inches and/or about 0.95-1.2 inches are suitable, for example, about 1.05 inches. For the centrifugal separator having a maximum flowrate of 30 gpm, ranges of about 4.0-6.0 inches and/or about 4.9-5.3 inches are suitable, for example, about 5.1 inches.

Centrifugal separators RPM (for both the aqueous base washing operation and the water washing operation): For the centrifugal separator having a maximum flowrate of 0.5 gpm, a range of about 1000-5000 RPM is suitable, for example, about 3500 RPM. For the centrifugal separator having a maximum flowrate of 30 gpm, ranges of about 800-3500 RPM and/or about 1800-2200 RPM are suitable, for example, about 1900 RPM.

Flow rate for both the aqueous base washing operation and the water washing operation): In principal, better phase separation performance was expected for lower flow rates. For the centrifugal separator having a maximum flowrate of 0.5 gpm, ranges of about 0.5-2.5 l/min and/or about 1.2-1.8 l/min are suitable. For the centrifugal separator having a maximum flowrate of 30 gpm, ranges of about 5-30 gal/min and/or about 10-14 gal/min are suitable, for example, about 12 gal/min.

In-line mixer length (for both the aqueous base washing operation and the water washing operation): the length of the in-line mixer did not significantly affect phase separation performance, but should be sufficient to allow sufficient mixing and contact time to allow conversion of HFIP to its corresponding salt and extraction of the HFIP salt into the aqueous phase in the aqueous base washing operation and extraction of any residual base into the water in the water washing operation. For both models of centrifugal separator, a range of about 4 to 72 inches is suitable for the in-line mixer length. The total in-line mixer length can be adjusted by incorporating different numbers of in-line mixers into the system.

The mixing and contact time can be relatively short in the methods according to the invention and still be sufficient to perform the wash operation. For example, for the aqueous base washing operation, the mixing and contact time can be between about 3-50 seconds depending on the length of in-line mixer(s) and the flow rate of the crude sevoflurane and the aqueous base through the in-line mixer(s) and still be sufficient to convert substantially all of the HFIP into the HFIP-salt and allow extraction of the salt into the aqueous phase.

The following example is provided to illustrate the disclosure, but are not intended to limit the scope thereof.

EXAMPLE 1

A lab-scale system was used to purify crude sevoflurane according to the methods of the invention. The system utilized was substantially as shown in FIG. 1. Crude sevoflurane was first flash distilled and then purified according to the methods according to the invention using the following apparatus and process parameters. After the crude sevoflurane was processed according to the methods according to the invention, the sevoflurane was again distilled.

Equipment: A centrifugal separator having a maximum flowrate of 0.5 gpm was used. The organic pump had a Masterflex™ L/S Precision Variable-Speed Drive and a Masterflex™ L/S Easy-Load™ II pump head for high performance precision tubing having GORE Style 500 Tubing (Cole-Palmer). The aqueous base pump had a Masterflex™ L/S Precision Variable-Speed Drive and a Masterflex™ L/S Easy-Load™ II pump head for high performance precision tubing having Masterflex™ PharMed BPT Tubing (Cole-Palmer). The in-line mixer for mixing the aqueous base and crude sevoflurane was a Koflo® in-line static mixer ¾" NPT, 0.742" I.D., perfluoroalkoxy alkane (PFA) (Cole-Palmer). The in-line mixer length was 72" for mixing the aqueous base and the crude sevoflurane and 6" for mixing water and the sevoflurane (after separation of the sevoflurane from the aqueous base in the first centrifugal separator).

Process parameters: centrifugal separator RPM: 3500; heavier phase weir size: 1.05 inches; flow rate: 1.2 L/min; sevoflurane to aqueous base (NaOH, 10 wt.%) volume ratio: 2:1.

COMPARATIVE EXAMPLE 1

Crude sevoflurane was first flash distilled (as in Example 1) and then further purified using a method incorporating various purification steps disclosed in the prior art discussed in the Background section above. Specifically, subsequent to flash distillation, the crude sevoflurane was washed with caustic solution to dissolve and remove unreacted HFIP from the crude sevoflurane. Thereafter, the phases were separated and the organic phase was washed with fresh water. Then, the organic phase was again separated from the aqueous phase and the sevoflurane was distilled to further purify the sevoflurane. The two washing operations were conducted step-wise in two (different) mixing tanks and the phase separations were manually controlled. Each washing operation contained several steps including charging the mixing tanks with the organic and aqueous phases, mixing the organic and aqueous phases, allowing the phases to settle, separating the organic phase from the aqueous phase, and transferring the aqueous phase stream and the washed organic phase stream into corresponding storage tanks. For each of the washing operations, and because efficient extraction and partitioning between the aqueous and organic phases requires significant mixing, several hours were typically required for charging, mixing, and settling.

Results for the purification of crude sevoflurane according to Example 1 are provided in Table I, below, and are contrasted with results for the method of purifying sevoflurane described in Comparative Example 1. Subsequent to purification according to Example 1 and Comparative Example 1, the purified sevoflurane was distilled.

TABLE I

| Results | Compound A content in feed subsequent to purification steps (before final distillation) | Final Distillation Cycle Time | Final Distillation Yield (%) distillation and final distillation | Processing time between flash |
|---|---|---|---|---|
| Comparative Example 1 | ~300 ppm | 53 hr | 61% | >4 hours |
| Example 1 | Not detectable (<10 ppm) | 34 hr | 81% | <20 seconds |

As demonstrated by the above results, purifying sevoflurane according to the methods according to the invention produced substantially pure sevoflurane and minimized the formation of compound A. Because compound A is the number one contributing factor affecting the final distillation yield and cycle time, the methods according to the invention advantageously facilitate pharmaceutical-grade sevoflurane production in less time and in high yield and purity relative to existing sevoflurane purification processes.

What is claimed:

1. A method of purifying crude sevoflurane comprising:
   (i) providing crude sevoflurane and an aqueous base to a first centrifugal separator, wherein the crude sevoflurane comprises sevoflurane and hexafluoroisopropanol;
   (ii) mixing the crude sevoflurane and the aqueous base in the first centrifugal separator; and
   (iii) separating the sevoflurane from the aqueous base in the first centrifugal separator, thereby purifying the crude sevoflurane.

2. The method of purifying crude sevoflurane according to claim 1, further comprising:
   (iv) providing the sevoflurane from (iii) and water to a second centrifugal separator;
   (v) mixing the sevoflurane and the water in the second centrifugal separator; and
   (vi) separating the sevoflurane from the water in the second centrifugal separator, thereby purifying the crude sevoflurane.

3. The method of purifying crude sevoflurane according to claim 1, further comprising:
   (iv) providing the sevoflurane from (iii) and water to an in-line mixer; and,
   (v) mixing the sevoflurane and the water in the in-line mixer to form a mixture.

4. The method of purifying crude sevoflurane according to claim 3, further comprising:
   (vi) providing the mixture to a second centrifugal separator; and (vii) separating the sevoflurane from the water in the second centrifugal separator.

5. The method of purifying crude sevoflurane according to claim 4, further comprising distilling the sevoflurane to ensure production of and obtain pharmaceutical-grade sevoflurane.

6. The method of purifying crude sevoflurane according to claim 5, wherein the pharmaceutical-grade sevoflurane contains less than 10 ppm compound A.

7. The method of purifying crude sevoflurane according to claim 1, wherein the aqueous base comprises one or more water-soluble bases selected from the group consisting of sodium hydroxide, potassium hydroxide, calcium hydroxide, ammonium hydroxide, and combinations thereof.

8. The method of purifying crude sevoflurane according to claim 1, wherein the aqueous base comprises up to 50 weight percent sodium hydroxide.

9. A method of purifying crude sevoflurane comprising:
   (i) providing crude sevoflurane and an aqueous base to a first in-line mixer, wherein the crude sevoflurane comprises sevoflurane and hexafluoroisopropanol;
   (ii) mixing the crude sevoflurane and the aqueous base in the first in-line mixer to form a first mixture;
   (iii) providing the first mixture to a first centrifugal separator; and
   (iv) separating the sevoflurane from the aqueous base in the first centrifugal separator, thereby purifying the crude sevoflurane.

10. The method of purifying crude sevoflurane according to claim 9, further comprising:
    (v) providing the sevoflurane from (iv) and water to a second in-line mixer; and,
    (vi) mixing the sevoflurane and the water in the second in-line mixer to form a second mixture.

11. The method of purifying crude sevoflurane according to claim 10, further comprising:
    (vii) providing the second mixture to a second centrifugal separator; and
    (viii) separating the sevoflurane from the water in the second centrifugal separator.

12. The method of purifying crude sevoflurane according to claim 9, further comprising:
    (v) providing the sevoflurane from (iv) and water to a second centrifugal separator;
    (vi) mixing the sevoflurane and the water in the second centrifugal separator;
    (vii) separating the sevoflurane from the water in the second centrifugal separator.

13. The method of purifying crude sevoflurane according to claim 9, further comprising distilling the sevoflurane to ensure production of and obtain pharmaceutical-grade sevoflurane.

14. The method of purifying crude sevoflurane according to claim 13, wherein the pharmaceutical-grade sevoflurane contains less than 10 ppm compound A.

15. The method of purifying crude sevoflurane according to claim 9, wherein the aqueous base comprises one or more water-soluble bases selected from the group consisting of sodium hydroxide, potassium hydroxide, calcium hydroxide, ammonium hydroxide, and combinations thereof.

16. The method of purifying crude sevoflurane according to claim 9, wherein the aqueous base comprises up to 50 weight percent sodium hydroxide.

* * * * *